United States Patent
Lu et al.

(10) Patent No.: US 10,258,584 B2
(45) Date of Patent: Apr. 16, 2019

(54) PREGABALIN SUSTAINED-RELEASE PREPARATION

(71) Applicant: Jiangsu Hengrui Medicine Co., Ltd., Lianyungang, Jiangsu (CN)

(72) Inventors: Yun Lu, Jiangsu (CN); Jiajia Xu, Jiangsu (CN); Hao Chen, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 6 days.

(21) Appl. No.: 15/519,661

(22) PCT Filed: Sep. 24, 2015

(86) PCT No.: PCT/CN2015/090511
§ 371 (c)(1),
(2) Date: Apr. 17, 2017

(87) PCT Pub. No.: WO2016/062182
PCT Pub. Date: Apr. 28, 2016

(65) Prior Publication Data
US 2017/0239203 A1    Aug. 24, 2017

(30) Foreign Application Priority Data
Oct. 24, 2014  (CN) .......................... 2014 1 0578204

(51) Int. Cl.
| | | |
|---|---|---|
| *A61K 31/197* | (2006.01) | |
| *A61K 47/10* | (2017.01) | |
| *A61K 47/32* | (2006.01) | |
| *A61K 47/36* | (2006.01) | |
| *A61K 47/02* | (2006.01) | |
| *A61K 9/00* | (2006.01) | |
| *A61K 9/06* | (2006.01) | |
| *A61K 9/20* | (2006.01) | |

(52) U.S. Cl.
CPC .......... *A61K 31/197* (2013.01); *A61K 9/0053* (2013.01); *A61K 9/0065* (2013.01); *A61K 9/06* (2013.01); *A61K 9/205* (2013.01); *A61K 9/2031* (2013.01); *A61K 47/02* (2013.01); *A61K 47/10* (2013.01); *A61K 47/32* (2013.01); *A61K 47/36* (2013.01); *A61K 9/2009* (2013.01); *A61K 9/2018* (2013.01); *A61K 9/2027* (2013.01)

(58) Field of Classification Search
None
See application file for complete search history.

(56) References Cited

FOREIGN PATENT DOCUMENTS

| | | |
|---|---|---|
| CN | 101330907 A | 12/2008 |
| CN | 103585098 A | 2/2014 |
| CN | 103702664 A | 4/2014 |
| EP | 2389934 A1 * | 11/2011 |

OTHER PUBLICATIONS

The Second Method (Paddle Method) of the Dissolution Test Disclosed in the Appendix of vol. II of Chinese Pharmacopeia (2010).
Huang et al, "Types of Oral Controlled Release Preparation," Acta Pharmaceutica Sinica, vol. 21, No. 2, pp. 152-157 (Dec. 31, 1986).
Int'l Search Report dated Dec. 30, 2015 in Int'l Application No. PCT/CN2015/090511.

* cited by examiner

*Primary Examiner* — Savitha M Rao
*Assistant Examiner* — Gregg Polansky
(74) *Attorney, Agent, or Firm* — Panitch Schwarze Belisario & Nadel LLP

(57) ABSTRACT

Disclosed is a pregabalin sustained-release preparation, wherein the sustained-release tablet contains a pharmaceutically active ingredient containing pregabalin or a salt or hydrate thereof, a gel framework material containing alginic acid, and a swellable material containing polyoxyethylene.

20 Claims, 1 Drawing Sheet

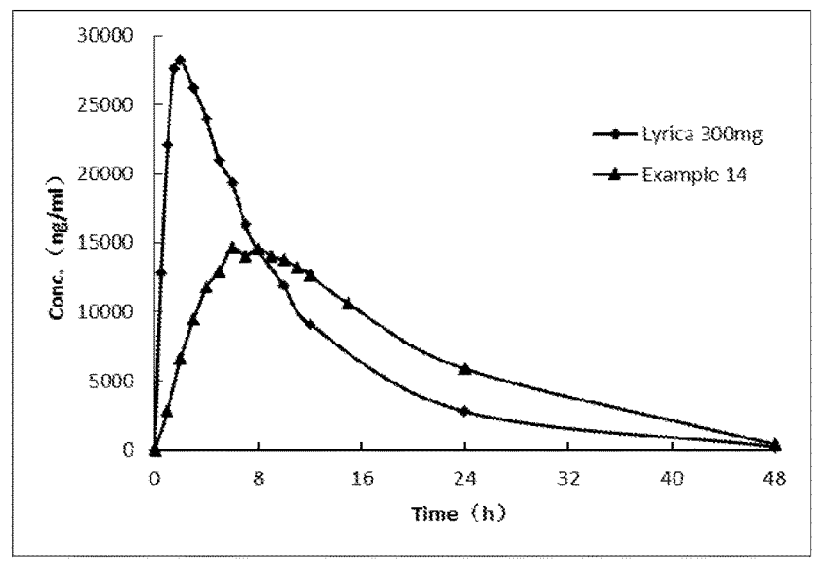

PREGABALIN SUSTAINED-RELEASE PREPARATION

CROSS-REFERENCE TO RELATED APPLICATION

This application is a Section 371 of International Application No. PCT/CN2015/090511, filed Sep. 24, 2015, which was published in the Chinese language on Apr. 28, 2016 under International Publication No. WO 2016/062182 A1, and the disclosure of which is incorporated herein by reference.

FIELD OF THE INVENTION

The present invention relates to the field of pharmaceutical preparations, and in particular relates to a pregabalin sustained-release preparation, which provides for controlled release of the drug within a window for a patient to obtain an effective therapeutic effect.

BACKGROUND OF THE INVENTION

Pregabalin, having the chemical name (S)-(+)-3-aminomethyl-5-methyl-hexanoic acid, is a novel calcium channel modulator (a non γ-butyric acid (GABA) receptor agonist or antagonist), which can block voltage-dependent calcium channels and reduce the release of neurotransmitters. Clinically, it is mainly used for the treatment of peripheral neuropathic pain and for the adjunctive treatment of partial-onset seizures. The current dosage form of pregabalin is the immediate release (IR) dosage form in tablets and capsules mostly, with specifications of 25, 50, 75, 100, 150, 200 and 300 mg/capsule (or tablet), and is administered 2-3 times per day.

A sustained-release preparation developed for once daily can improve patients' drug compliance, reduce or prevent dose-related adverse reactions (by reducing maximum blood concentration $C_{max}$), and improve efficacy (by increasing the maintenance time of effective blood concentration). However, there are some problems in developing a dosage form of pregabalin for once daily administration. Since pregabalin is absorbed through the L-amino acid delivery system, it does not show uniform gastrointestinal absorption. Clinical studies indicate that pregabalin is well absorbed in the small intestine and the ascending colon, but is poorly absorbed after the hepatic flexure. This suggests that the average absorption window of pregabalin is six hours or less, and if developed into a conventional sustained-release preparation, the drug will be wasted and cannot exert any effect when it is transferred to the hepatic flexure about 6 hours after administration. Obviously, for a drug having such an absorption window, it is important to design an effective sustained-release preparation that not only releases the drug at a controlled rate, but also retains the drug in the upper gastrointestinal tract for a long time.

Natural compounds have gained more and more attention due to their good biocompatibility and biodegradability, and are used in various fields from medicine and health products to food additives. Alginic acid is a natural polymer present in brown algae or bacteria, and consists of β-D-mannuronate and α-L-guluronate. The natural marine resources are abundant in China, and the output of alginate is at the forefront of the world. Alginate is widely used in the field of pharmaceutical science, because alginate has a carboxyl group that allows it to adapt to different chemical microenvironments. Alginate can form a gel layer at low pH (i.e., in a gastric fluid environment), which can prolong the residence time of the drug in the stomach by using the properties of alginate to form a swelling gel, thereby increasing the absorption window of certain drugs and improving the bioavailability of the drug. Water-soluble alginate and calcium salt present in the tablet simultaneously can quickly form an acid-insoluble gel matrix of calcium alginate with good strength when the tablet is administered orally and contacts gastric juice, and the drug contained therein is slowly released. At the same time, a gastric retention drug delivery system can also prolong the transit time of the drug along the entire length of the gastrointestinal tract by retaining the drug in the stomach, thereby improving the bioavailability of the drug.

Patent application publication no. CN101330907A discloses a sustained-release preparation for once daily oral administration comprising pregabalin, a matrix forming agent and a swelling agent. The preparation induces the gastric retention of pregabalin by size change after swelling. However, the preparation has a certain burst-release effect, which is not conducive for controlling the slow and stable release of the drug. Also, the size of the preparation after rapid swelling is not significantly greater than the diameter of the human pylon's, such that the possibility of passing through the pylorus cannot be excluded depending on patients' respective gastrointestinal conditions, thereby resulting in failure to show sustained release patterns. Another disadvantage is that the matrix rigidity of the preparation is significantly decreased after 24 hours. Patent application publication no. CN103702664A relates to a pregabalin sustained-release tablet having a two-phase controlled-release system, but the scale up is not easy due to the use of the wet granulation process in the preparation procedure, and there is a certain risk of product consistency after the scale up. Patent CN application publication no. 103585098A discloses a controlled-release preparation containing pregabalin and a preparation method thereof. However, since the preparation is not in a form for gastric retention, it may result in the release of pregabalin not only in the upper part of the small intestine (the main absorption site of pregabalin), but also at other sites, such as the lower part of the small intestine.

SUMMARY OF THE INVENTION

It is an object of the present invention to provide a pregabalin sustained-release preparation comprising alginate as a gel matrix to achieve long-lasting release and absorption of the drug, and to improve the bioavailability of the drug by prolonging the residence time in the stomach.

The sustained-release tablet provided by the present invention comprises an active pharmaceutical ingredient and excipients. The active pharmaceutical ingredient includes pregabalin, or a pharmaceutically acceptable complex, salt, solvate or hydrate thereof, and the excipients include a gel matrix material and a swelling material. The gel matrix material includes alginate, and the swelling material includes polyoxyethylene.

The alginate used in the present invention may be one or more of sodium alginate, potassium alginate, and ammonium alginate. The average molecular weight of the alginate can be $1 \times 10^4$ to $2 \times 10^5$ daltons, preferably $7 \times 10^4$ to $15 \times 10^4$ daltons. The amount of the gel matrix material is about 5% to 45% by weight, preferably about 20% to 40% by weight, based on the total weight of the sustained-release tablet.

For oral solid dosage forms, the gel matrix material provides structural integrity and helps to control or prolong the rate of drug release and other functions. Alginate can form a gel layer at low pH (i.e., in a gastric environment), which can prolong the residence time of the drug in the stomach by using the properties of alginate to form a swelling gel, thereby increasing the absorption window of certain drugs and improving the bioavailability of the drug.

The swelling material can absorb water from the gastric fluid and swell several times its original volume, resulting in the gastric retention of the sustained-release tablets due to size exclusion, and can also affect the drug release rate by forming a hydrophilic colloid. The swelling material can be soluble or insoluble in water. The amount of the swelling material is about 10% to 75%, preferably 30% to 60%, more preferably 35% to 60% by weight, based on the total weight of the sustained-release tablet. The swelling materials of the present invention include polyoxyethylene, also known as polyethylene oxide and polyethylene glycol. The molecular weight of the polyoxyethylene can be $1 \times 10^5$ to $1 \times 10^7$, preferably $1 \times 10^6$ to $1 \times 10^7$.

In a preferred embodiment of the present invention, in addition to the alginate, the gel matrix material further comprises a calcium salt. Water-soluble alginate reacts with calcium ions to quickly form a thermally irreversible gel matrix with good gel strength. The calcium salt used in the present invention can be one or more of calcium hydrogen phosphate, calcium dihydrogen phosphate, calcium phosphate, calcium bisulfate, calcium bisulfite, calcium sulfate, calcium bicarbonate, calcium carbonate, and calcium chloride. In the gel matrix material, the weight ratio of the alginate to the calcium salt is from 1:1 to 10:1, preferably from 2:1 to 5:1. In a preferred embodiment of the present invention, the gel matrix material consists of the alginate and the calcium salt.

In a preferred embodiment of the present invention, in addition to polyoxyethylene, the swelling material can further include crosslinked polyvinylpyrrolidone, also known as crospovidone. The molecular weight of the crosslinked polyvinylpyrrolidone can be about $1 \times 10^3$ to $1 \times 10^7$, preferably about $1 \times 10^4$ to about $1 \times 10^5$. When the polyoxyethylene is used in combination with the crosslinked polyvinylpyrrolidone, the sustained-release preparation typically comprises polyoxyethylene present in amount of about 25% to 55% by weight, based on the total weight of the preparation, and crosslinked polyvinylpyrrolidone present in amount of 5% to 20% by weight, based on the total weight of the preparation, preferably polyoxyethylene present in amount of 30% to 50%, based on the total weight of the preparation, and crosslinked polyvinylpyrrolidone present in amount of 5% to 10% by weight, based on the total weight of the preparation.

The sustained-release preparation of the present invention can comprise one or more lubricants to aid in mixing the components and tabletting. The amount of the lubricant is about 0.5% to 2% by weight, based on the total weight of the sustained-release preparation. The lubricant includes talc, magnesium stearate, zinc stearate, glyceryl behenate, sodium lauryl sulfate, hydrogenated vegetable oils, colloidal silicon dioxide and the like.

The sustained-release preparation of the present invention can include other excipients, such as a diluent, present in an amount of about 0% to 20% by weight, based on the weight of the sustained-release tablet. The diluent may improve the flowability of the pharmaceutical composition and may enhance the compression strength or hardness of the tablet during the procedure of mixing the components and tabletting. The diluent includes lactose, mannitol, starch, pregelatinized starch, microcrystalline cellulose and the like.

In a preferred embodiment of the present invention, the sustained-release preparation is a tablet.

According to the present invention, a pharmaceutical composition is prepared by dry mixing a drug with a gel matrix material, a swelling material, a lubricant, and other excipients, and then the pharmaceutical composition is directly compressed into tablets. Alternatively, to improve product homogeneity, the components can be combined and mixed in stages. For example, the drug can be first dry mixed with one or more gel matrix materials, while other excipients, such as a swelling materials, a diluent, a lubricant, and the like, can be subsequently mixed in one or more mixing operations. If desired, the particle size of one or more components can be controlled by sieving or grinding or both prior to mixing. The compressed tablet can be coated with a conventional coater.

When an in vitro dissolution test of the sustained-release preparation of the present invention is carried out, the release amount of the active ingredient (i.e., pregabalin) is less than 15% within 1 hour; the release amount (cumulative dissolution rate) is 50 to 70% at 4 to 8 hours; and the release amount (cumulative dissolution rate) is more than 80% at 16 hours. When administered orally, the sustained-release tablet according to the present invention is effective in controlling the release of pregabalin along with showing a controlled and prolonged release profile without showing the initial burst-release effect.

The sustained-release preparation of the present invention can swell or expand to 13 mm or more when contacted with water present in human gastric fluid. Furthermore, the shape and rigidity of the preparation were well maintained after being contacted with water, thereby exhibiting a more excellent gastric retention. The sustained-release tablet can be retained in the stomach for several hours by size exclusion, administration with a meal, administration before bedtime, or a combination of these methods. The residence time of the sustained-release tablet of the present invention in the patient's stomach is usually about 3 hours to 11 hours, about 6 hours to 14 hours, or about 8 hours to 14 hours, thereby maximizing the absorption of pregabalin in the upper part of the small intestine.

The time to the maximum plasma concentration (Tmax) can be 8 hours to 12 hours after oral administration of the sustained-release preparation of the present application. In the sustained-release preparation of the present invention, the release of pregabalin is controlled by the gel matrix material and the swelling material. The release time and gastric retention characteristics are controlled by varying the amounts of the gel matrix material and the swelling material. Thus, the sustained-release preparation of the present invention can be administered once daily by controlling the release matrix of pregabalin to have a limited absorption window.

DESCRIPTION OF THE DRAWINGS

FIG. 1 is a graph showing the mean plasma concentration vs. time for the sustained-release tablet prepared according to the present invention (Example 14) in comparison to a commercially available Lyrica® immediate-release capsule.

DETAILED DESCRIPTION OF THE INVENTION

The present invention will be described in more detail by the following examples and experimental examples. These examples and experimental examples are for illustrative purposes only and are not intended to limit the scope of the present invention.

Examples 1 to 20

Sustained-release tablets were prepared according to the components and amounts shown in Tables 1 to 3. The amounts in Table 1 to Table 3 represent the weight (mg) of each component in each tablet. For each example, all of the tablet components except magnesium stearate were mixed in a material mixer for about 15 minutes, and then mixed with magnesium stearate that was passed through a 20 mesh sieve for a further 5 minutes to obtain a final blend. The final blend was then compressed in a tablet press to obtain tablets of 1.125 g or 1 g in weight.

TABLE 1

| Components | Example (mg/tablet) | | | | |
|---|---|---|---|---|---|
| | 1 | 2 | 3 | 4 | 5 |
| Pregabalin | 300 | 300 | 300 | 300 | 300 |
| Sodium alginate | 338 | 281 | 225 | 225 | 225 |
| polyoxyethylene (Polyox 303) | 476 | 420 | 420 | 363 | 363 |
| CaHPO$_4$ | — | — | — | — | 113 |
| CaCO$_3$ | — | — | — | — | — |
| Crospovidone | — | — | — | — | — |
| Lactose | — | 113 | 169 | 226 | 113 |
| Magnesium stearate | 11 | 11 | 11 | 11 | 11 |
| Total | 1125 | 1125 | 1125 | 1125 | 1125 |

| Components | Example (mg/tablet) | | | |
|---|---|---|---|---|
| | 6 | 7 | 8 | 9 |
| Pregabalin | 300 | 300 | 300 | 300 |
| Sodium alginate | 225 | 282 | 282 | 282 |
| polyoxyethylene (Polyox 303) | 363 | 363 | 363 | 390 |
| CaHPO$_4$ | 113 | 56 | — | 86 |
| CaCO$_3$ | — | — | 56 | — |
| Crospovidone | 56 | 113 | 113 | 56 |
| Lactose | 56 | — | — | — |
| Magnesium stearate | 11 | 11 | 11 | 11 |
| Total | 1125 | 1125 | 1125 | 1125 |

TABLE 2

| Components | Example (mg/tablet) | | | | | |
|---|---|---|---|---|---|---|
| | 10 | 11 | 12 | 13 | 14 | 15 |
| Pregabalin | 330 | 330 | 330 | 330 | 330 | 330 |
| Sodium alginate | 225 | 282 | 196 | 225 | 282 | 282 |
| polyoxyethylene (Polyox 303) | 363 | 390 | 363 | 390 | 363 | 390 |
| CaHPO$_4$ | — | — | 56 | 113 | 56 | 56 |
| Crospovidone | 83 | 113 | 56 | 56 | 83 | 56 |
| Lactose | 113 | — | 113 | — | — | — |
| Magnesium stearate | 11 | 11 | 11 | 11 | 11 | 11 |
| Total | 1125 | 1126 | 1125 | 1125 | 1125 | 1125 |

TABLE 3

| Components | Example (mg per one tablet) | | | | | |
|---|---|---|---|---|---|---|
| | 16 | 17 | 18 | 19 | 20 | 21 |
| Pregabalin | 165 | 165 | 165 | 82.5 | 82.5 | 82.5 |
| Sodium alginate | 352 | 260 | 280 | 250 | 300 | 280 |
| polyoxyethylene (Polyox 303) | 323 | 410 | 390 | 507.5 | 447.5 | 467.5 |
| CaHPO$_4$ | 50 | 55 | 55 | 50 | 60 | 60 |
| Crospovidone | 100 | 100 | 100 | 100 | 100 | 100 |
| Magnesium stearate | 10 | 10 | 10 | 10 | 10 | 10 |
| Total | 1000 | 1000 | 1000 | 1000 | 1000 | 1000 |

Comparative Example 1

The comparative example was prepared according to patent application publication no. CN101330907A. As shown in Table 4, pregabalin (300 g), Kollidon SR (250 g), Plasdone XL (280 g), Polyox N60K NF (225 g) and Carbopol 71 G (56.5 g) were mixed for 15 minutes. The above mixture was additionally mixed with magnesium stearate (11.5 g) for 5 minutes, and then compressed to obtain tablets.

TABLE 4

| Components | Comparative Example 1 | |
|---|---|---|
| | %, w/w | mg per one tablet |
| pregabalin | 26.7 | 300 |
| KOLLIDON ® SR | 22.3 | 250 |
| PLASDONE ® XL | 25.0 | 282 |
| POLYOX ® WSR N60K NF | 20.0 | 225 |
| CARBOPOL ® 71G | 5.0 | 56.5 |
| Magnesium stearate | 1.0 | 11.5 |
| Total | 100.0 | 1125 |

Experimental Example 1: In Vitro Dissolution Test

The tablets prepared in Examples 1 to 21 and Comparative Example 1 were subjected to a dissolution test according to the second method (paddle method) of the dissolution test disclosed in the appendix of volume II of Chinese Pharmacopeia (2010 edition). 1000 ml of a 0.06 N HCl solution was used as a dissolution medium, and the dissolution test was carried out at 37±0.5° C. and at the paddle speed of 50 rpm. Small samples were taken from the dissolution medium at 0.5, 1, 2, 4, 8, 12, 16, 20 and 24 hours, respectively. Each sample was analyzed with HPLC (at 210 nm) to calculate the dissolution rate. The results are shown in Tables 5 to 7.

As shown in Tables 5 to 7, the pregabalin preparations prepared according to the present invention showed excellent sustained-release dissolution patterns. The pregabalin sustained-release preparations had essentially no burst-release effect at 1 hour, the dissolution amount was 50% to 70% at 8 hours, and the release amount was more than 80% at 16 hours by adjusting the components and ratios of the sustained-release preparations. The tablets prepared in Comparative Example 1 had a cumulative dissolution rate of about 20% at 1 hour, which showed a certain burst-release effect, whereas the tablets prepared according to the present invention significantly weakened this burst-release effect, thereby releasing pregabalin more slowly, and increasing the safety of the drug.

TABLE 5

| Time (h) | Example (dissolution rate, %) | | | | | | | | | Comparative Example 1 |
|---|---|---|---|---|---|---|---|---|---|---|
| | 1 | 2 | 1 | 4 | 5 | 6 | 7 | 8 | 9 | |
| 0.5 | 6.0 | 6.9 | 7.3 | 7.6 | 8.9 | 6.8 | 6.9 | 8.5 | 6.1 | 11.6 |
| 1 | 10.3 | 15.3 | 18.2 | 19.1 | 18.4 | 12.4 | 11.1 | 13.6 | 10.9 | 19.3 |
| 2 | 16.9 | 19.7 | 25.4 | 24.7 | 23.7 | 20.3 | 20.2 | 23.3 | 23.9 | 29.1 |
| 4 | 28.7 | 30.4 | 34.1 | 36.4 | 35.0 | 35.9 | 39.6 | 38.4 | 41.2 | 43.8 |
| 8 | 52.1 | 55.6 | 56.8 | 58.8 | 54.6 | 59.1 | 64.6 | 62.6 | 68.1 | 67.6 |
| 12 | 69.8 | 73.6 | 75.2 | 76.3 | 76.8 | 79.9 | 80.8 | 83.3 | 85.3 | 79.5 |
| 16 | 78.9 | 81.3 | 85.3 | 87.2 | 88.4 | 88.8 | 90.8 | 94.5 | 92.5 | 88.6 |
| 20 | 86.1 | 87.3 | 89.5 | 91.9 | 91.3 | 95.1 | 94.8 | 98.2 | 95.0 | 92.7 |
| 24 | 90.6 | 91.7 | 93.6 | 96.0 | 95.7 | 97.3 | 96.6 | 98.5 | 96.2 | 96.8 |

TABLE 6

| Time (h) | Example (dissolution rate, %) | | | | | |
|---|---|---|---|---|---|---|
| | 10 | 11 | 12 | 13 | 14 | 15 |
| 0.5 | 8.1 | 8.0 | 8.5 | 7.3 | 10.5 | 7.7 |
| 1 | 13.2 | 12.8 | 13.4 | 12.5 | 16.5 | 11.6 |
| 2 | 20.6 | 23.6 | 22.5 | 21.2 | 24.2 | 21.2 |
| 4 | 37.6 | 42.5 | 39.2 | 35.5 | 38.7 | 34.2 |
| 8 | 63.2 | 65.6 | 61.3 | 59.3 | 60.9 | 58.1 |
| 12 | 81.5 | 80.3 | 79.1 | 77.5 | 78.8 | 76.3 |
| 16 | 89.6 | 91.1 | 88.5 | 86.5 | 87.2 | 85.0 |
| 20 | 95.5 | 94.5 | 92.2 | 91.1 | 91.2 | 90.0 |
| 24 | 96.6 | 96.0 | 94.5 | 94.0 | 94.2 | 95.2 |

TABLE 7

| Time (h) | Example (dissolution rate, %) | | | | | |
|---|---|---|---|---|---|---|
| | 16 | 17 | 18 | 19 | 20 | 21 |
| 0.5 | 4.3 | 8.5 | 6.3 | 12.4 | 5.9 | 9.1 |
| 1 | 8.4 | 14.5 | 12.7 | 19.1 | 10.6 | 13.9 |
| 2 | 13.9 | 23.9 | 21.7 | 28.2 | 18.7 | 23.1 |
| 4 | 27.1 | 39.4 | 35.0 | 45.4 | 32.7 | 38.4 |
| 8 | 49.2 | 61.9 | 61.0 | 66.0 | 61.1 | 61.4 |
| 12 | 67.3 | 73.6 | 77.1 | 79.6 | 77.9 | 75.5 |
| 16 | 81.3 | 84.4 | 86.9 | 87.4 | 90.5 | 83.7 |
| 20 | 86.4 | 88.7 | 93.2 | 89.0 | 92.0 | 88.8 |
| 24 | 91.4 | 93.8 | 97.0 | 90.6 | 93.2 | 93.3 |

Experimental Example 2: Measurement of Swelling Size

The tablets prepared in the above Examples and Comparative Example were subjected to a dissolution test according to the second method (paddle method) of the dissolution test disclosed in the appendix of volume II of Chinese Pharmacopeia (2010 edition). 1000 ml of a 0.06 N HCl solution was used as a dissolution medium, and the dissolution test was carried out at 37±0.5° C. and at a paddle speed of 50 rpm. The drug samples were taken out from the dissolution medium at 1, 2, 6, 8 and 24 hours after the start of the dissolution test and then their sizes were measured. The results are shown in Tables 8 and 9. The size of the tablets prepared according to the present invention swelled to 13 mm or more at 1 hour (the "size" corresponds to the longest linear size of the cross-section having the smallest area of the dosage form), and the residence time of the sustained-release tablet in the stomach can be effectively prolonged by mechanical retardation of the size. The size of the tablets prepared in Comparative Example 1 swelled to only 11.4 mm at 1 hour, and the possibility of passing through the pylorus could not be excluded according to the gastrointestinal condition of the patient.

TABLE 8

| Time (h) | Example 1 | Example 7 | Comparative Example 1 |
|---|---|---|---|
| 0 | 19.6 × 10.0 × 8.5 | 19.6 × 10.0 × 8.5 | 19.4 × 9.7 × 8.8 |
| 1 | 22.5 × 13.0 × 11.5 | 23.4 × 13.7 × 12.4 | 20.5 × 11.4 × 9.9 |
| 2 | 23.4 × 13.7 × 12.8 | 24.8 × 14.3 × 13.0 | 21.1 × 12.2 × 11.4 |
| 6 | 25.0 × 14.6 × 14.3 | 25.9 × 14.8 × 14.4 | 22.7 × 13.3 × 12.5 |
| 8 | 26.2 × 15.0 × 14.6 | 26.8 × 15.6 × 14.9 | 23.1 × 13.5 × 12.6 |
| 24 | 26.9 × 15.8 × 15.3 | 27.6 × 16.2 × 15.6 | 23.7 × 14.0 × 12.8 |

TABLE 9

| Time (h) | Example 14 | Example 17 | Example 20 |
|---|---|---|---|
| 0 | 19.6 × 10.0 × 8.5 | 19.5 × 10.3 × 7.8 | 19.5 × 10.3 × 7.9 |
| 1 | 23.4 × 13.6 × 12.0 | 23.4 × 13.3 × 11.6 | 23.0 × 13.8 × 11.8 |
| 7 | 23.8 × 14.5 × 13.0 | 24.3 × 13.7 × 13.0 | 24.2 × 13.5 × 13.0 |
| 6 | 25.7 × 14.8 × 14.0 | 25.1 × 14.5 × 13.7 | 25.0 × 14.3 × 13.6 |
| 8 | 264 × 15.3 × 14.5 | 25.8 × 14.8 × 14.0 | 25.9 × 14.6 × 13.9 |
| 24 | 27.0 × 16.2 × 15.1 | 27.1 × 14.9 × 14.0 | 27.0 × 15.0 × 14.0 |

Experimental Example 3: Comparison of Changes in Size and Water Content of Tablets The tablets prepared in Examples 1 and 7 and Comparative Example 1 were subjected to a dissolution test according to the second method (paddle method) of the dissolution test disclosed in the appendix of volume II of Chinese Pharmacopeia (2010 edition). 1000 ml of a 0.06 N HCl solution was used as a dissolution medium, and the dissolution test was carried out at 37±0.5° C. and at the paddle speed of 50 rpm. The drug samples were taken out from the dissolution medium at 1, 2, 6, 8 and 24 hours after the start of the dissolution test, their sizes were measured, and the weight change of each tablet was obtained by measuring its water content. The results are shown in Table 10.

As shown in Table 10, the tablets prepared in Examples 1 and 7 exhibited better properties regarding size change and water content, in comparison to the tablet of Comparative Example 1. These results indicate that the tablets of the present invention can more effectively increase the residence time in the stomach, thereby achieving a long-lasting release and absorption effect of the drug and improving the bioavailability of the drug.

TABLE 10

|  | Example 1 | | Example 7 | | Comparative Example 1 | |
| --- | --- | --- | --- | --- | --- | --- |
| Time (h) | Weight change (%) | Size change (%) | Weight change (%) | Size change (%) | Weight change (%) | Size change (%) |
| 1 | 163 | 202 | 179 | 239 | 108 | 139 |
| 2 | 191 | 246 | 226 | 277 | 136 | 177 |
| 6 | 236 | 313 | 252 | 331 | 170 | 228 |
| 8 | 258 | 344 | 286 | 374 | 183 | 237 |
| 24 | 277 | 366 | 318 | 419 | 197 | 256 |

Experimental Example 4: Comparison of Drug Rigidity

The tablets prepared in Example 7 and Comparative Example 1 were subjected to a dissolution test according to the second method (paddle method) of the dissolution test disclosed in the appendix of volume II of the Chinese Pharmacopeia (2010 edition). 1000 ml of a 0.06 N HCl solution was used as a dissolution medium, and the dissolution test was carried out at 37±0.5° C. and at a paddle speed of 50 rpm. The drug samples were taken out from the dissolution medium at 1, 2, 6, 8 and 24 hours after the start of the dissolution test, and their rigidity was measured using a TA-Plus texture analyzer under the following setting conditions: 5 kg load unit; P/0.5 cylindrical probe; 1.0 g trigger force; 1.0 mm/s test speed; and 15 mm distance. The results are shown in Table 11.

As shown in Table 11, the tablets prepared according to the present invention (Example 1 and Example 7) had better rigidity and still showed good rigidity after swelling for 8 hours and 24 hours, in comparison to the tablets of Comparative Example 1. The excellent rigidity provided good gastric retention characteristics, but was also effective in controlling the release of pregabalin.

TABLE 11

| Time | Gel Rigidity (g mm) | | |
| --- | --- | --- | --- |
| (h) | Example 1 | Example 7 | Comparative Example 1 |
| 1 | 4923 | 4876 | 4654 |
| 2 | 4205 | 4135 | 4023 |
| 6 | 2783 | 2568 | 1734 |
| 8 | 2457 | 1934 | 1086 |
| 24 | 1363 | 876 | 105 |

Experimental Example 5: Measurement of Dissolution Rate According to Paddle Speed The tablets prepared in Examples 1, 7 and Comparative Example 1 were subjected to a dissolution test according to the second method (paddle method) of the dissolution test disclosed in the appendix of volume II of the Chinese Pharmacopeia (2010 edition). 1000 ml of a 0.06 N HCl solution was used as a dissolution medium, and the dissolution test was carried out at 37±0.5° C. and at paddle speeds of 50 rpm and 100 rpm, respectively. Small samples were taken from the dissolution medium at 0.5, 1, 2, 4 and 8 hours, respectively. Each sample was analyzed with HPLC (at 210 nm) to calculate the dissolution rate. The results are shown in Table 12.

TABLE 12

| Dissolution rates at 50 rpm and 100 rpm | | | | | |
| --- | --- | --- | --- | --- | --- |
| Example 1 | | Example 7 | | Comparative Example 1 | |
| 50 rpm | 100 rpm | 50 rpm | 100 rpm | 50 rpm | 100 rpm |
| 0.5 | 6.0 | 6.8 | 6.9 | 8.1 | 11.6 | 19.6 |
| 1 | 10.3 | 12.1 | 11.1 | 14.4 | 18.3 | 26.5 |
| 2 | 16.9 | 18.8 | 20.2 | 22.5 | 29.1 | 37.8 |
| 4 | 28.7 | 30.5 | 39.6 | 41.8 | 43.8 | 51.0 |
| 8 | 52.1 | 55.2 | 64.6 | 67.3 | 67.6 | 76.2 |

As shown in Table 12, the tablets of Example 1 and Example 7 showed relatively small differences in the dissolution rate when the paddle speed was increased. In contrast, the dissolution rate, particularly the initial dissolution rate, of the tablet of Comparative Example 1 was significantly increased when the paddle speed was increased. These results indicate that the tablets of the present invention are less affected by the rotational speed of the paddle plate. Therefore, the tablets of the present invention are less affected by gastrointestinal motility, thereby minimizing individual differences.

Experimental Example 6: Pharmacokinetic Study

The pharmacokinetic study of the tablet prepared in Example 14 was carried out using beagle dogs. The commercially available Lyrica® Capsule 300 mg (Pfizer Pharmaceutical Co., Ltd.) was used as a reference preparation. The concentration of pregabalin in plasma was determined by liquid chromatography-tandem mass spectrometry. The plasma concentration curve is shown in FIG. 1; and the pharmacokinetic parameters are shown in Table 13.

TABLE 13

| Pharmacokinetic parameters | Reference preparation (Lyrica ® Cap. 300 mg) | Example 14 |
| --- | --- | --- |
| $AUC_{0-24\,h}$ (µg · h/ml) | 320.8 | 318.2 |
| $C_{max}$ (µg/ml) | 30.3 | 17.7 |
| $T_{max}$ (h) | 1.9 | 10.5 |

The sustained-release tablet of Example 14 showed delayed absorption in comparison to the immediate release tablet of the reference preparation. In Example 14, the average peak time $T_{max}$ to the maximum plasma concentration of the prototype drug pregabalin in dogs was 10.5 h, which was significantly later than that of the reference preparation group (1.9 h); the peak concentration ($C_{max}$) was approximately 60% of that of the reference preparation after administration; and the relative bioavailability was 99.2%. Since pregabalin is absorbed in the upper part of the small intestine, the sustained-release tablets of the present invention can remain in the stomach for a longer period of time, but can still effectively control the release of pregabalin.

What is claimed is:

1. An oral sustained-release preparation comprising pregabalin, a salt or hydrate thereof as an active ingredient, a gel matrix material and a swelling material, wherein the gel matrix material comprises alginate, and the swelling material comprises polyoxyethylene, wherein a release amount of the active ingredient is less than 15% within 1 hour and more than 80% at 16 hours as determined by an in vitro dissolution test of the oral sustained-release preparation.

2. The oral sustained-release preparation according to claim 1, wherein the preparation is for oral administration once daily.

3. The oral sustained-release preparation according to claim 1, wherein the alginate is at least one selected from the group consisting of sodium alginate, potassium alginate, and ammonium alginate.

4. The oral sustained-release preparation according to claim 1, wherein the amount of the gel matrix material is 5% to 45% by weight, based on a total weight of the sustained-release preparation.

5. The oral sustained-release preparation according to claim 1, wherein the amount of the swelling material is 10% to 75% by weight, based on a total weight of the sustained-release preparation.

6. The oral sustained-release preparation according to claim 1, wherein the average molecular weight of the alginate is $1 \times 10^4$ to $2 \times 10^5$ Da.

7. The oral sustained-release preparation according to claim 1, wherein the average molecular weight of the polyoxyethylene is $1 \times 10^5$ to $1 \times 10^7$ Da.

8. The oral sustained-release preparation according to claim 1, wherein the gel matrix material further comprises a calcium salt.

9. The oral sustained-release preparation according to claim 8, wherein a weight ratio of the alginate to the calcium salt is 1:1 to 10:1.

10. The oral sustained-release preparation according to claim 1, wherein the swelling material further comprises crosslinked polyvinylpyrrolidone.

11. The oral sustained-release preparation according to claim 10, wherein the swelling material consists of polyoxyethylene and crosslinked polyvinylpyrrolidone.

12. An oral sustained-release preparation comprising pregabalin, a salt or hydrate thereof as an active ingredient, a gel matrix material and a swelling material, wherein the gel matrix material comprises alginate and a calcium salt, and the swelling material comprises polyoxyethylene and crosslinked polyvinylpyrrolidone, and wherein a weight ratio of the alginate to the calcium salt is 1:1 to 10:1, the polyoxyethylene is present in an amount of 10% to 55% by weight, based on a total weight of the preparation, and the crosslinked polyvinylpyrrolidone is present in an amount of 5% to 20% by weight, based on the total weight of the preparation.

13. The oral sustained-release preparation according to claim 1, wherein the sustained-release preparation has a size of 13 mm or greater upon being contacted with water for 1 hour.

14. The oral sustained-release preparation according to claim 1, wherein the sustained-release preparation is retained in the stomach of a patient for 3 hours to 14 hours after oral administration.

15. The oral sustained-release preparation according to claim 1, wherein the time to the maximum plasma concentration ($T_{max}$) is 8 hours to 12 hours after oral administration of the sustained-release preparation.

16. The oral sustained-release preparation according to claim 4, wherein the amount of the gel matrix material is 20% to 40% by weight, based on the total weight of the sustained-release preparation.

17. The oral sustained-release preparation according to claim 5, wherein the amount of the swelling material is 30% to 60% by weight, based on the total weight of the sustained-release preparation.

18. The oral sustained-release preparation according to claim 8, wherein the calcium salt is at least one selected from the group consisting of calcium hydrogen phosphate, calcium phosphate, calcium bisulfate, calcium sulfate, calcium bicarbonate, calcium carbonate, and calcium chloride.

19. The oral sustained-release preparation according to claim 9, wherein the weight ratio of the alginate to the calcium salt is 2:1 to 5:1.

20. An oral sustained-release preparation comprising pregabalin, a salt or hydrate thereof as an active ingredient, a gel matrix material and a swelling material, wherein the gel matrix material comprises alginate and a calcium salt, and the swelling material comprises polyoxyethylene and crosslinked polyvinylpyrrolidone, and wherein a weight ratio of the alginate to the calcium salt is 2:1 to 5:1, the polyoxyethylene is present in an amount of 30% to 50% by weight, based on a total weight of the preparation, and the crosslinked polyvinylpyrrolidone is present in an amount of 5% to 10% by weight, based on the total weight of the preparation.

* * * * *